United States Patent [19]

Dzwonkiewicz

[11] Patent Number: 5,562,078

[45] Date of Patent: Oct. 8, 1996

[54] ENDOTRACHEAL TUBE/STETHOSCOPE CONNECTOR

[76] Inventor: Mark Dzwonkiewicz, 578 Somerset #3, Crystal Lake, Ill. 60014

[21] Appl. No.: 468,644

[22] Filed: Jun. 6, 1995

[51] Int. Cl.$^6$ .................................................. A61M 16/00
[52] U.S. Cl. .............................. 128/207.18; 128/207.14; 128/207.16; 128/204.23; 128/202.27
[58] Field of Search ......................... 128/200.24, 202.13, 128/202.16, 202.27, 205.23, 204.23, 207.14, 207.15, 207.16, 207.17, 207.18, 911, 912, DIG. 26; 181/131, 137

[56] References Cited

U.S. PATENT DOCUMENTS

| | | | |
|---|---|---|---|
| 4,919,127 | 4/1990 | Pell | 128/207.14 |
| 5,056,514 | 10/1991 | DuPont | 128/207.14 |
| 5,287,851 | 2/1994 | Beran et al. | 128/204.23 |
| 5,309,905 | 5/1994 | Tevel | 128/207.14 |

Primary Examiner—Vincent Millin
Assistant Examiner—V. Seivastava
Attorney, Agent, or Firm—Thomas R. Vigil

[57] ABSTRACT

According to the present invention there if provided a connector comprising a generally hollow body having a cross section that varies over the length of the body, having a distal end sized to fit over and connect with the proximal end of an endotracheal tube and having a larger proximal end that includes structure for releasably connecting to a diaphragm end of a stethoscope.

11 Claims, 3 Drawing Sheets 5,562,078

ENDOTRACHEAL TUBE/STETHOSCOPE CONNECTOR

BACKGROUND OF THE INVENTION

1. Field of the Invention

The present invention relates to a connector for connecting the proximal end of an endotracheal tube to a stethoscope thereby to enable a physician to clearly hear breath-sounds through the endotracheal tube.

2. Description of the Related Art Including Information Disclosed under 37 CFR §§ 1.97–1.99.

Heretofore, various types of endotracheal tube connectors have been proposed and set forth below are analogous and nonanalogous U.S. Patents disclosing various types of endotracheal tube connectors.

| U.S. Pat. No. | Patentee |
| --- | --- |
| 4,369,991 | Linder |
| 4,607,643 | Bell et al. |
| 4,919,127 | Pell |
| 5,056,514 | DuPont |
| 5,251,617 | Linder |

The most pertinent of these prior art patents is the DuPont U.S. Pat. No. 5,056,514 which discloses an endotracheal stethoscope. As shown in FIG. 2 of this patent, an inline connector or T-shaped tube member is connected into a line between the proximal end of an endotracheal tube and a tube or hose leading to a anaesthesia/breathing machine. A drum member of a stethoscope is connected to the stem portion of the T. A thin flexible membrane is stretched tightly across the lower end of the drum member.

As will be described in greater detail hereinafter, the connector of the present invention is generally funnel or conically shaped having a lower end adapted to be connected to the proximal end of an endotracheal tube and a wider upper end which is adapted to be connected to a standard diaphragm of a standard stethoscope. Preferably the conical side wall of the connector has an opening which can be opened and closed by the thumb of the physician, nurse or paramedic attending the patient.

SUMMARY OF THE INVENTION

According to the present invention there is provided a connector comprising a generally hollow body having an elongate, a distal end, a proximal end and a cross section that increases over the length of the body from the distal end to the proximal end, the distal end being sized to fit over and connect with the proximal end of an endotracheal tube, the proximal end being in-line with the distal end on and along the elongate axis and the proximal end of the connector having a short, inwardly, extending annular flange for enabling the proximal end of the connector to be received snap fittingly over the diaphragm of a stethoscope.

DESCRIPTION OF THE PREFERRED EMBODIMENT(S)

Figure 1:
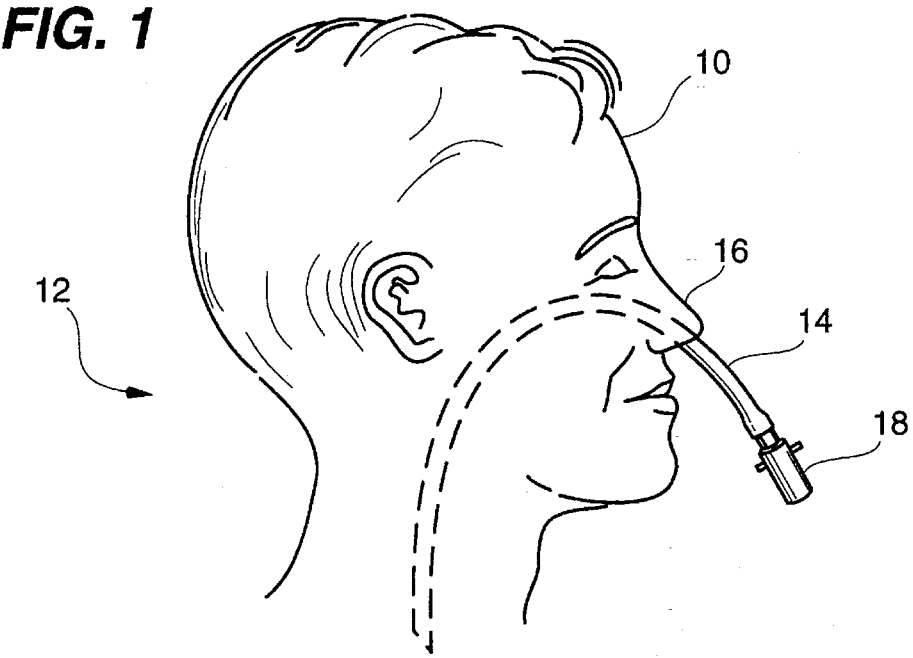
FIG. 1 is side elevational view of the head of a patient having an endotracheal tube inserted through the patient's nose and into the throat of the patient.
Figure 2:
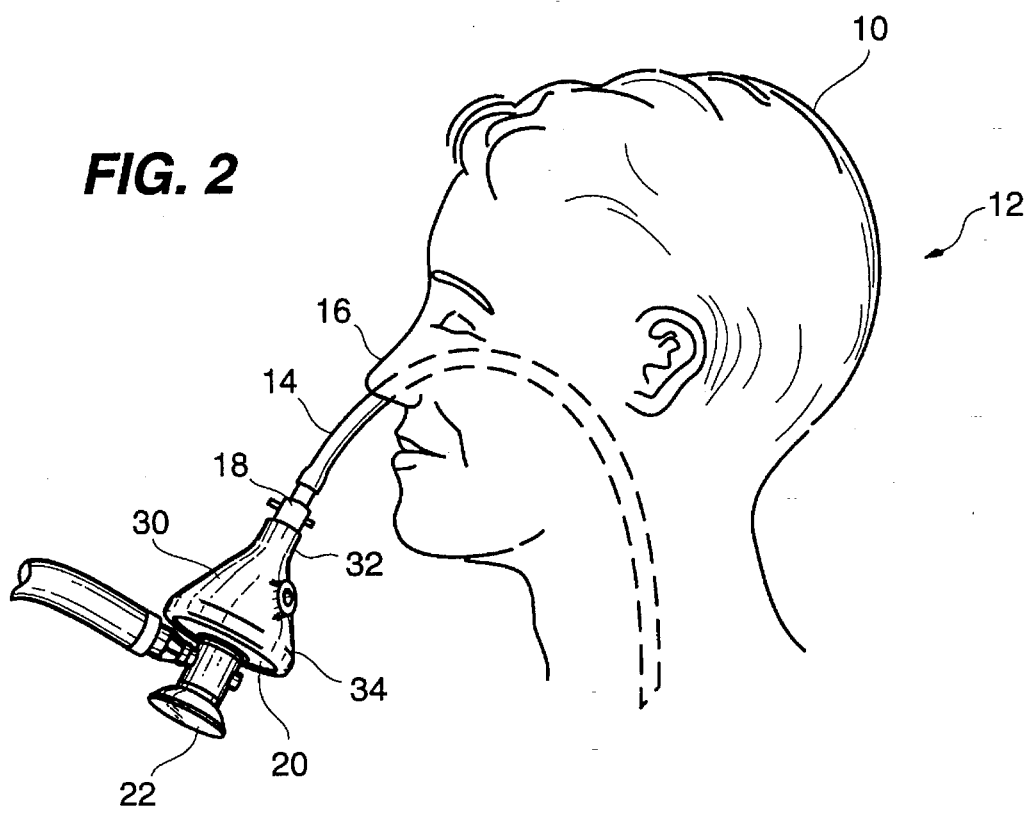
FIG. 2 is a opposite side elevational view of the endotracheal tube shown in FIG. 1 including a connector constructed according to the teachings of the present invention connected to the proximal end of the endotracheal tube and a stethoscope diaphragm connected to the proximal end of the connector.

Referring now to FIGS. 1 and 2 there is illustrated therein the head 10 of a patient 12 having an endotracheal tube 14 inserted through the nose 16 of the patient and into the throat of the patient. A proximal end 18 of the endotracheal tube 14 is shown extending from the nose 16 of the patient 12.

In emergency situations such as at the scene of an automobile accident, it is very common to perform an intubation procedure where such an endotracheal tube 14 is inserted into a patient to insure breathing of the patient and to provide a clear path to the patient's lungs. At that time it is also desirable to be able to hear the breath-sounds of the patient which can be accomplished most easily by placing the diaphragm 20 of a stethoscope 22 into communication with the endotracheal tube 14.

However, the proximal end 18 of the endotracheal tube 14 is much smaller than the diameter of the conventional diaphragm 20 of the stethoscope 22 and it is difficult sometimes for a doctor, nurse or paramedic to use the stethoscope 22 to hear the breath-sounds of the patient through the endotracheal tube 14.

According to the teachings of the present invention, a connector 30 is provided which is connected at its distal end 32 to the proximal end 18 of the endotracheal tube 14 and at its proximal end 34 to the diaphragm portion 20 of the stethoscope 22.

With the connector 30 of the present invention, a physician, nurse or paramedic can easily connect the connector 30 to the proximal end 18 of the endotracheal tube 14 and releasably connect the diaphragm end 20 of the stethoscope 22 to the connector 30 for listening to the patient's breath-sounds.

Figure 3:
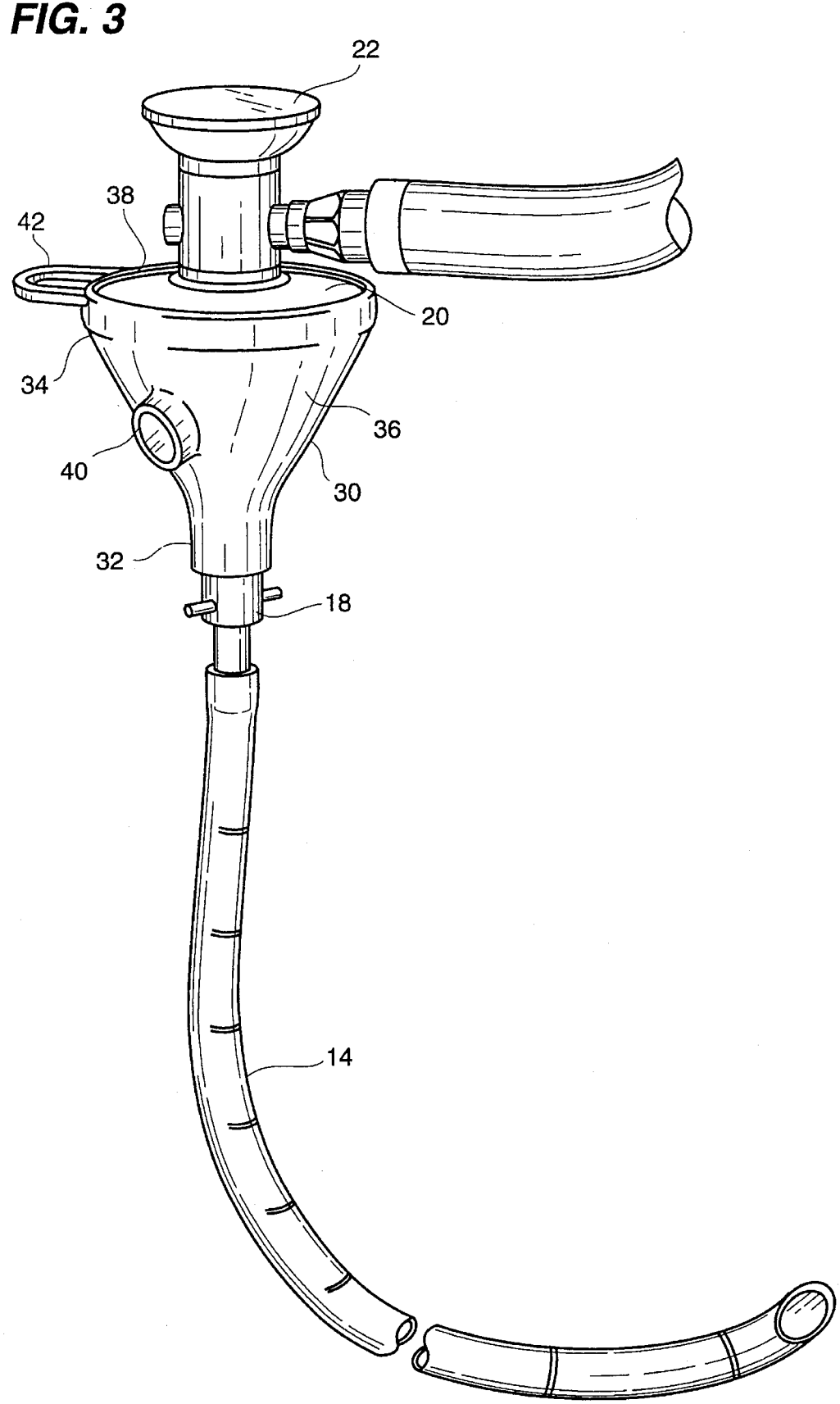
FIG. 3 is an enlarged perspective view of the diaphragm end of a stethoscope releasably fixed to the proximal end of the connector of the present invention and shows the distal end of the connector connected to the proximal end of an endotracheal tube.
Figure 4:
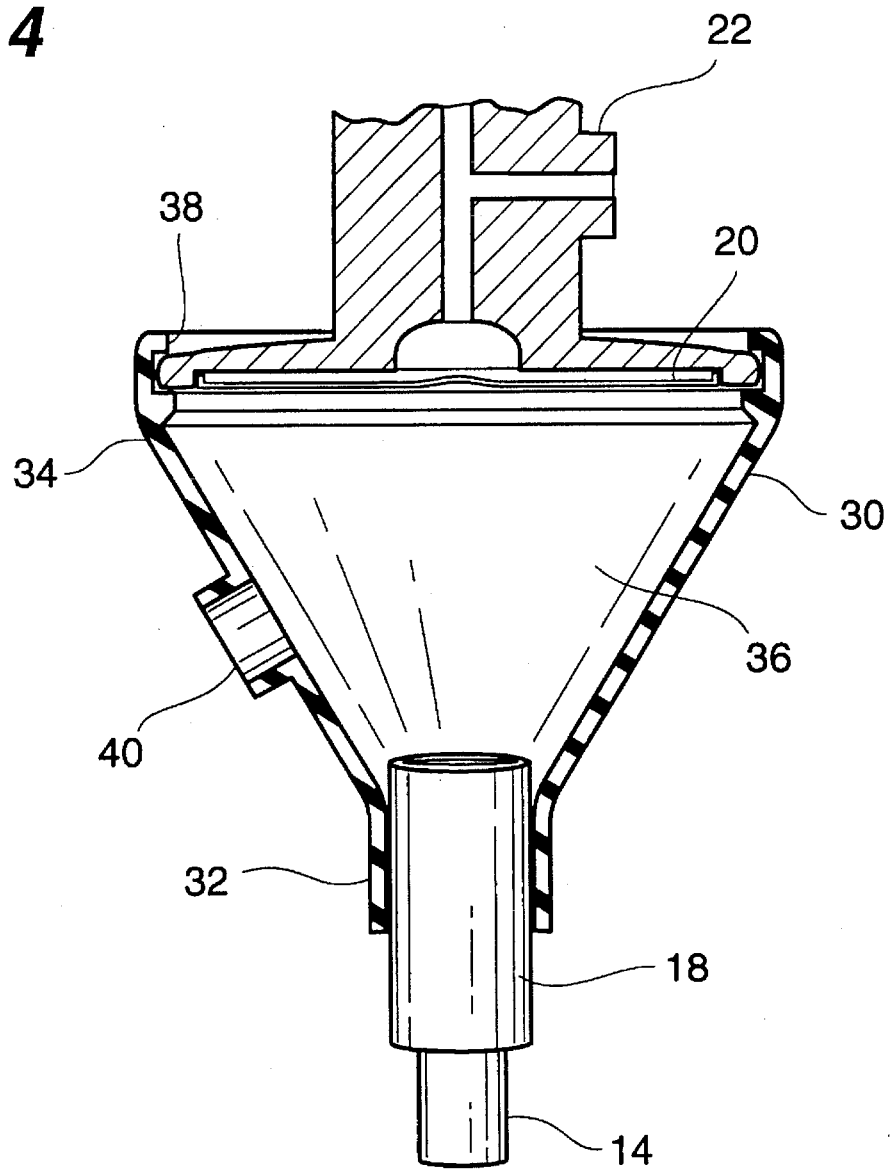
FIG. 4 is a cross-sectional view of the connector shown in FIG. 3.

As best shown in FIGS. 3 and 4 the connector 30 includes a hollow body 36 which can be made of metal or plastic and preferably made of plastic and has a generally conical shape. Then the body 36 tapers conically from the proximal end 34 which if desired can have a short inwardly extending annular flange 38 for snap fitting over the diaphragm 20 of the stethoscope 22. From there, the body 36 tapers to its distal end 32 which is generally cylindrical and which is adapted to be frictionally received over the proximal end 18 of the endotracheal tube 14.

Also provided is a vent hole 40 in the side of the body 36 which has an inner diameter approximately the same as the inner diameter of the proximal end 18 of the endotracheal tube 14.

Further a small tab 42 can be provided at the proximal end 34 of the body 36 to facilitate holding of the connector 30 while the stethoscope 22 is pulled away and detached from the connector 30.

In use a medical technician such as a nurse, doctor or paramedic will listen to the breath-sounds with the stethoscope 22 and at the same time hold a finger such as the thumb over the vent hole 40 and periodically open the vent hole 40 to insure proper placement of endotracheal tube 14.

Typically the body 36 will be 1/16" to 1/8" thick and have an outer diameter at its proximal end 34 of approximately 1 3/4" to 1 13/16". In this way the proximal end 34 of the connector body 36 can easily mount a stethoscope 22 having a 1 1/2" diaphragm 20. The body 36 then tapers in a conical fashion to the cylindrical distal end portion 32 which has an inner diameter of approximately 9/16" for being frictionally received over the proximal end 18 of the endotracheal tube 14 which has an outer diameter of approximately 9/16" and an inner diameter of approximately 7/16".

The vent hole 40 also has a inner diameter of approximately 7/16".

From the foregoing description, it will be apparent that the connector 30 of the present invention has a number of advantages, some of which have been described above and others of which are inherent in the connector 30 of the present invention. In particular the connector 30 of the present invention enables a medical technician such as a nurse, doctor or paramedic to easily hear the breath-sounds of a patient through an endotracheal tube 22 that has been inserted through an intubation procedure into a patient. Then the connector 30 can be easily disconnected from the proximal end 18 of the endotracheal tube 14 which can then be connected to a breathing or aspiration machine.

This is particularly useful and important where the patient is being treated in a noisy environment and it is important to be able to quickly and accurately listen to the breath-sounds of the patient.

Also from the foregoing description, it will be apparent that modifications can be made to the connector 30 of the present invention without departing from the teachings of the present invention. In this respect the body 36 can have a different shape other than a conical shape so long as it has a cylindrical distal end for releasably and frictionally connecting to the proximal end of an endotracheal tube and a larger proximal end for releasably connecting to a diaphragm of a stethoscope.

Accordingly, the scope of the invention is only to be limited as necessitated by the accompanying claims.

I claim:

1. A connector comprising a generally hollow body having an elongate axis, a distal end, a proximal end and a cross section that increases over the length of said body from said distal end to said proximal end, said distal end being sized to fit over and connect with the proximal end of an endotracheal tube, said proximal end being in-line with said distal end on and along said elongate axis and said proximal end of said connector having a short, inwardly, extending annular flange for enabling said proximal end of said connector to be received snap fittingly over the diaphragm of a stethoscope.

2. The connector of claim 1 wherein said body is generally conical in shape.

3. The connector of claim 1 wherein said body has a thickness of between 1/16" and 1/8".

4. The connector of claim 1 wherein said distal end of said connector is generally cylindrical and has an inner diameter sized to frictionally fit over the proximal end of an endotracheal tube.

5. The connector of claim 1 wherein the inner diameter of the cylindrical distal end of said connector is approximately 9/16" in diameter.

6. The connector of claim 1 having a vent opening on the side of said body with an inner diameter at least as large as the inner diameter of the proximal end of the endotracheal tube.

7. The connector of claim 6 wherein said vent hole has an inner diameter of approximately 7/16".

8. The connector of claim 1 wherein said proximal end of said connector has an outer diameter of between 1 3/4" and 1 13/16".

9. A connector comprising a hollow body having a distal end sized to fit over and connect with the proximal end of an endotracheal tube and having a proximal end having means for releasably connecting to a diaphragm end of a stethoscope, and said proximal end of said connector having a short, inwardly, extending annular flange for enabling said proximal end of said connector to be received snap fittingly over the diaphragm of a stethoscope.

10. A connector comprising a generally, hollow, conical body having an elongate axis, a distal end and a proximal end, said distal end being sized to fit over and connect with the proximal end of an endotracheal tube, said proximal end being in-line with said distal end on and along said elongate axis and said proximal end of said connector having a short, inwardly, extending annular flange for enabling said proximal end of said connector to be received snap fittingly over the diaphragm of a stethoscope.

11. A connector comprising a generally hollow body having an elongate axis, a distal end, a proximal end and a cross section that increases over the length of said body from said distal end to said proximal end, said distal end being sized to fit over and connect with the proximal end of an endotracheal tube inserted into a patient, said larger proximal end including means for releasably connecting to a diaphragm end of a stethoscope, said proximal end being in-line with said distal end on and along said elongate axis, and said hollow body having a hand coverable vent opening located on a side of said body and having an inner diameter at least as large as the inner diameter of the proximal end of the endotracheal tube and adapted to be covered by a user's hand for facilitating listening to the patient's breath sounds with a stethoscope connected to said proximal end of said connector and to be uncovered when not listening to the patient's breath sounds to facilitate breathing of the patient.

* * * * *